United States Patent
Baker et al.

(10) Patent No.: US 11,413,112 B2
(45) Date of Patent: Aug. 16, 2022

(54) RADIOPAQUE TISSUE MARKER

(71) Applicants: VISCUS BIOLOGICS, LLC, Cleveland, OH (US); THE CLEVELAND CLINIC FOUNDATION, Cleveland, OH (US)

(72) Inventors: Justin Jeffrey Baker, Gates Mills, OH (US); Peter Hayes Gingras, Shaker Heights, OH (US); Robert Priest, Twinsburg, OH (US); Kathe Derwin, Cleveland, OH (US); Joseph P. Iannotti, Cleveland, OH (US); Sambit Sahoo, Cleveland, OH (US); Andrew Ryan Baker, Cleveland, OH (US)

(73) Assignees: VISCUS BIOLOGICS, LLC, Cleveland, OH (US); THE CLEVELAND CLINIC FOUNDATION, Cleveland, OH (US)

( * ) Notice: Subject to any disclaimer, the term of this patent is extended or adjusted under 35 U.S.C. 154(b) by 338 days.

(21) Appl. No.: 16/160,229

(22) Filed: Oct. 15, 2018

(65) Prior Publication Data
US 2019/0110859 A1 Apr. 18, 2019

Related U.S. Application Data

(60) Provisional application No. 62/571,927, filed on Oct. 13, 2017.

(51) Int. Cl.
*A61B 90/00* (2016.01)

(52) U.S. Cl.
CPC ........ *A61B 90/39* (2016.02); *A61B 2090/392* (2016.02); *A61B 2090/3908* (2016.02);
(Continued)

(58) Field of Classification Search
CPC .... A61B 2090/3908; A61B 2090/3916; A61B 2090/392; A61B 2090/3937; A61B 2090/3966; A61B 90/39; A61F 2250/0098
See application file for complete search history.

(56) References Cited

U.S. PATENT DOCUMENTS

| | | | | |
|---|---|---|---|---|
| 5,610,967 A | * | 3/1997 | Moorman | A61B 6/06 378/154 |
| 6,174,330 B1 | * | 1/2001 | Stinson | A61B 17/12022 606/198 |

(Continued)

FOREIGN PATENT DOCUMENTS

WO WO-2017106474 A1 * 6/2017 .......... A61J 15/0015

OTHER PUBLICATIONS

The Apprentice Doctor, Surgical Suturing Techniques Mastery Guide, Mar. 11, 2015 (Year: 2015).*

(Continued)

*Primary Examiner* — Oommen Jacob
*Assistant Examiner* — Maria Christina Talty
(74) *Attorney, Agent, or Firm* — Tarolli, Sundheim, Covell & Tummino LLP (57) ABSTRACT

A fiber-based radiopaque tissue marker for radiographic marking of tissue is provided. The marker is a sterile, single-patient-use polymeric fiber with a radiopaque material and a dye. The marker is radiopaque using standard radiographs such as x-rays and mammography. The marker can also be visualized by low-dose CT scans.

15 Claims, 5 Drawing Sheets

(52) U.S. Cl.
CPC ............... *A61B 2090/3916* (2016.02); *A61B 2090/3937* (2016.02); *A61B 2090/3966* (2016.02); *A61F 2250/0098* (2013.01)

(56) References Cited

U.S. PATENT DOCUMENTS

| | | | | |
|---|---|---|---|---|
| 2005/0020916 | A1* | 1/2005 | MacFarlane | A61B 90/39 |
| | | | | 600/431 |
| 2007/0276494 | A1* | 11/2007 | Ferree | A61B 17/7053 |
| | | | | 623/17.11 |
| 2007/0288082 | A1* | 12/2007 | Williams | A61F 2/958 |
| | | | | 623/1.11 |
| 2008/0021313 | A1* | 1/2008 | Eidenschink | A61F 2/82 |
| | | | | 600/431 |
| 2011/0125253 | A1* | 5/2011 | Casanova | B29C 48/18 |
| | | | | 623/1.34 |
| 2012/0330153 | A1* | 12/2012 | Sirimanni | A61K 49/222 |
| | | | | 600/431 |
| 2013/0180966 | A1* | 7/2013 | Gross | A61B 17/06166 |
| | | | | 219/121.68 |
| 2015/0148837 | A1* | 5/2015 | Shinar | A61B 17/12145 |
| | | | | 606/200 |
| 2015/0297316 | A1* | 10/2015 | Grinstaff | A61B 10/04 |
| | | | | 600/414 |
| 2015/0327861 | A1* | 11/2015 | Jackson | A61L 17/00 |
| | | | | 606/224 |

OTHER PUBLICATIONS

Medical Plastics Data Service, "Effect of Sulphate as a Filler In Thermoplastic Polymer for Medical Applications", Jan. 2014 (Year: 2014).*
American Cancer Society, "Core Needle Biopsy of the Breast", Oct. 9, 2017 (Year: 2017).*
Ingle et al., "Mechanical Performance and Finite Element Analysis of Bi-directional Barbed Sutures," Aug. 2003, North Carolina State University, pp. 1-126 (Year: 2003).*
Jin-Cheol Kim et al., "Comparison of tensile and knot security properties of surgical sutures," Jun. 14, 2007, J Mater Sci: Mater Med, 18, pp. 2363-2369 (Year: 2007).*
Khiste, Sujeet Vinayak, V. Ranganath, and Ashish Sham Nichani. "Evaluation of tensile strength of surgical synthetic absorbable suture materials: an in vitro study " Journal of periodontal & implant science 43.3 (2013): 130.
Ethicon, Inc., "Knot Tying Manual", a Johnson and Johnson Company, 2005, PowerPoint Presentation, pp. 1-44.

* cited by examiner

RADIOPAQUE TISSUE MARKER

CROSS-REFERENCE TO RELATED APPLICATIONS

The present application claims priority to U.S. Provisional Application No. 62/571,927 filed on Oct. 13, 2017, which is incorporated by reference in its entirety herein.

TECHNICAL FIELD

The present disclosure relates to a radiopaque tissue marker that comprises a fiber that is visible using low dose radiation.

BACKGROUND

In the field of oncology, following biopsy of a suspected tumor or following surgical removal of the tumor, it is common practice to mark the biopsy site or lumpectomy site with a radiopaque marker that allows subsequent non-invasive imaging of the site. Many of the current tissue markers provide poor visibility during radiographic imaging, are subject to migration, have limited mechanical strength, and cannot be placed at a region of interest using standard surgical knots. For example, a tissue marker in the art has a fiber dimension of 1500×5000 microns and is configured as a small cylinder with perforations that is delivered through a needle. Such a marker is prone to migration and cannot outline a region of interest. Materials that include multifilament fibers or high surface area constructs can be more prone to inflammation and infection. In addition, existing tissue markers can obscure surrounding tissue areas radiographically due to the bloom effect or deflect/deform surrounding soft tissue due to their larger size. Some markers contain stiffer metals that can be felt by patients.

Methods of guided radiation therapy require accurate delivery of radiation. When delivering radiation therapy, it is important to accurately identify the tissue of interest at the time of treatment. If the tissue has an irregular shape, the ability to continuously mark/outline the region to permit accurate radiation therapy or identification during subsequent surgical procedures is critical.

SUMMARY

A radiopaque tissue marker is provided that allows for tissue to be marked and that is visible via radiographic imaging. A radiopaque tissue marker, as disclosed herein, provides favorable radiopacity, high tensile strength, and knot strength properties that permits placement in tissue to prevent migration. A radiopaque tissue marker, as disclosed herein, provides clinically relevant radiopacity while maintaining properties that permit delivery and permanent attachment to the tissue. A radiopaque tissue marker is disclosed that can be passed through tissue and secured with multiple suture knot throws with acceptable strength. Tensile strength is used herein as the force required to break a suture filament and is measured in Newtons (or pounds).

In certain aspects, a radiopaque tissue marker is a sterile polymeric fiber that is visible using low dose radiation. The fiber can have one or more of the following properties: a fiber diameter of approximately 300 microns to approximately 400 microns, a tensile strength greater than approximately 20 newtons (N); a knot strength greater than approximately 20N; and/or an elongation at rupture of less than approximately 50%.

In certain aspects, a method of outlining or marking a region of tissue is provided that includes obtaining a radiopaque tissue marker comprising a polymeric fiber having a diameter between about 300 to about 400 microns, a tensile strength greater than approximately 20 newtons (N); a knot strength greater than approximately 20N; and/or an elongation at rupture of less than approximately 50% and being visible using low dose radiation. The method further includes securing the radiopaque tissue marker in a region adjacent to a tissue of interest.

BRIEF DESCRIPTION OF THE DRAWINGS

FIG. 5A-5C are computer tomography (CT) images at three separate CT scan doses of human cadaver shoulder containing ten radiopaque tissue markers according to Example 1 of the present disclosure (1, 1b) and three CASSI BEACON tissue markers (2). FIG. 5A depicts a low-dose CT scan (100 kV, 45 mAs). FIG. 5B depicts a medium-dose CT scan (120 kV, 200 mAs); and FIG. 5C illustrates a high-dose CT scan (140 kV, 300 mAs).

DETAILED DESCRIPTION

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated.

Figure 1:
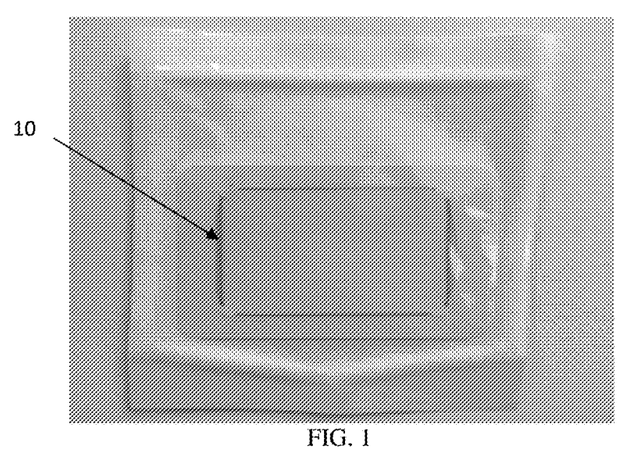
FIG. 1 is a top view of a radiopaque tissue marker in a sterile chevron pouch on a card holder according to an aspect of the present disclosure.

Referring to FIG. 1, the present disclosure relates to a fiber-based radiopaque tissue marker 10 for radiographic marking of tissue. The marker is a sterile polymeric fiber that is visible using low dose radiation. The fiber can have one or more of the following properties: a fiber diameter of approximately 300 microns to approximately 400 microns, a tensile strength greater than approximately 20 newtons (N); a knot strength greater than approximately 20N; and/or an elongation at rupture of less than approximately 50%.

Regarding the diameter of the fiber, a fiber diameter between approximately 300 microns to approximately 400 microns has a combination of favorable mechanical properties and radiopacity. The diameter of the fiber can be approximately 380 microns. A fiber having a diameter below approximately 300 microns has insufficient fiber strength such that tying a knot with the fiber is compromised. Further, a fiber diameter below approximately 300 microns has over approximately 40% less radiopaque material, which results in lower visibility of the fiber. A fiber having a diameter greater than approximately 400 microns has excessive stiffness such that tying a knot is difficult.

Regarding the tensile strength of the fiber, a fiber with tensile strength greater than approximately 20N has sufficient strength to permit the placement of tension on the fiber during securement in the tissue. The tensile strength of the fiber can be approximately 26 to 28 N. A fiber having a tensile strength below approximately 20 N has insufficient fiber strength such that placement in tissue with standard techniques and instruments is compromised.

Regarding the knot strength of the fiber, a fiber with knot strength greater than approximately 20N has sufficient strength to permit knotting of the fiber so as not to slip. Knots should be as small as possible in order to minimize the reaction to the foreign body material. Enough traction should remain on one end of the fiber to prevent it from loosening when tying the second throw. The knot strength of the fiber can be approximately 24 to 26 N. A fiber having a knot strength below approximately 20 N has insufficient knot strength such that placement in tissue with standard techniques and instruments is compromised.

Regarding the elongation of rupture of the fiber, a fiber with elongation at rupture less than approximately 50%, minimizes the risk of fiber distortion in the tissue. Fibers should limit elongation in order to minimize the risk of distortion during placement, knot tying, and under load in the body.

Figure 11:
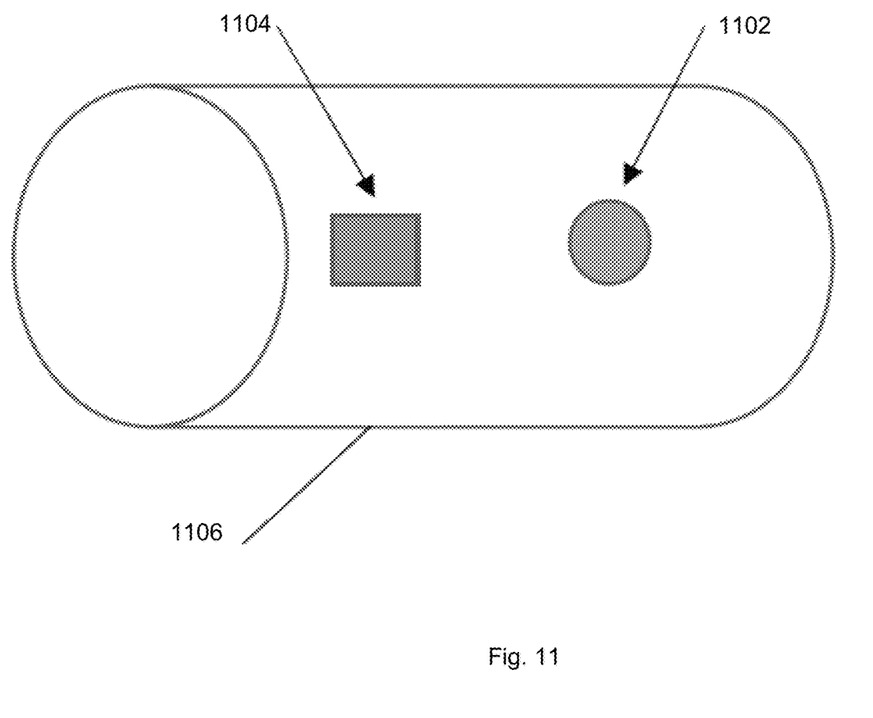
FIG. 11 illustrates a colorant or a radiopaque material disposed in a filament.

The fiber 1106 can comprise a polymer, a radiopaque material 1102, and a dye/colorant 1104 as illustrated in FIG. 11. Non-limiting examples of a polymer are polypropylene, polybutester, and nylon. In certain aspects, the only polymer in the radiopaque tissue marker is polypropylene. Non-limiting examples of a radiopaque material are barium sulfate, bismuth, tantalum, and iodine. In certain aspects, barium sulfate has a weight percentage greater than 40% in the radiopaque tissue marker. In certain aspects, the radiopaque material is not a radiopaque heavy metal. Non-limiting examples of a dye are a copper phthalocyanine blue, such as C.I. Pigment Blue 15:3.

The radiopaque tissue marker is radiopaque using standard radiographs such as, for example, x-ray and mammography. The tissue marker is also visible using low-dose computer tomography (CT) (LDCT) scans such as a CT scan performed at 100 kV and 45 mAs. Factors affecting dose in CT include tube voltage (kilovolt (kV)), tube current (milliampere (mA)), tube speed rotation (second (s)), the absorption of radiation by the human body (millisievert (mSv), which is a radioprotection unit measuring the radiation dose received either from a radioactive source), and slice thickness of individual slice images in a CT scan (millimeter (mm). Using either a kV or mAs range, a low dose CT can be performed at <=120 kV and/or <100 mAs. A recent study aimed at determining the distribution of effective dose associated with a single LDCT examination for lung cancer screenings, concluded that acceptable CT screening can be accomplished at an average effective dose of approximately 2 millisieverts (mSv). (See Larke F J, Kruger R L, Cagnon C H, et al. Estimated radiation dose associated with low-dose chest CT of average-size participants in the National Lung Screening Trial. AJR. 2011; 197:1165-1169). In examples provided below, imaging was performed at 0.6 mSv. The above ranges and values are considered "low dose" when used in CT scans. Since a CT scan is multiple sliced images that are combined to create a scan, a slice thickness of an individual slice image would influence the effective dose that the patient receives. In the examples provided below, the individual sliced images had a slice thickness of 0.6 mm.

Regarding mammography, the American Cancer Society defines a mammogram as a low-dose x-ray that allows radiologists to look for changes in breast tissue. See www.cancer.org/cancer/breast-cancer/screening-tests-and-early-det-ection/mammograms/mammogram-basics.html (Oct. 11, 2018)). As such, low-dose radiation, as used herein, includes mammography by definition. By way of illustration, mammography scans performed at 28 kV and 87 mAs; 26 kV and 69 mAs; and 28 kV and 92 mAs are considered low dose.

Figure 2:
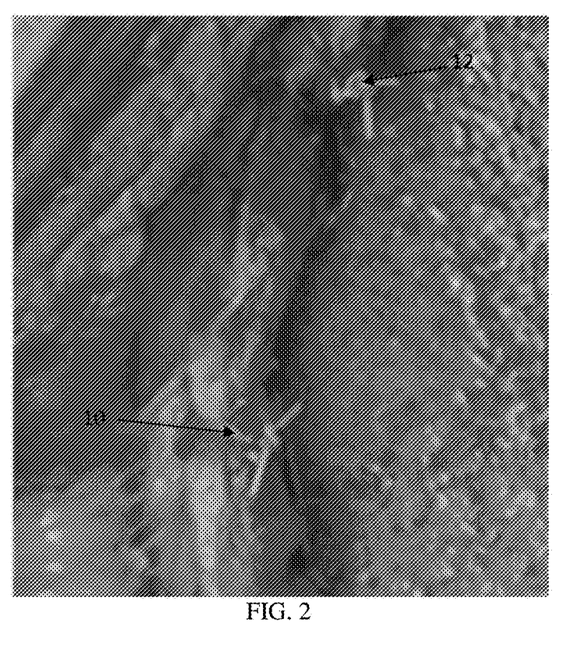
FIG. 2 is a photographic image of a radiopaque tissue marker sutured and knotted into tissue according to an aspect of the present disclosure.
Figure 7:
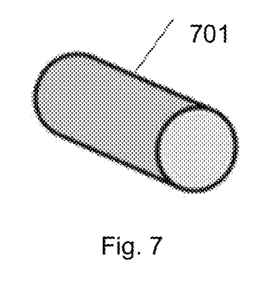
FIG. 7 illustrates a monofilament.
Figure 8:
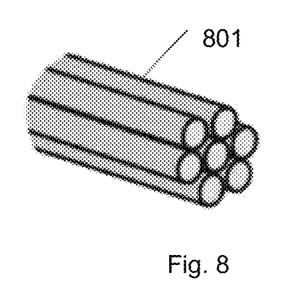
FIG. 8 illustrates a multi-filament.
Figure 9:
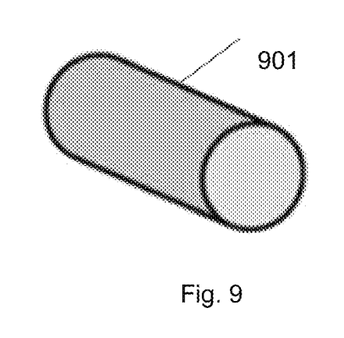
FIG. 9 illustrates a circular cross-section.
Figure 10:
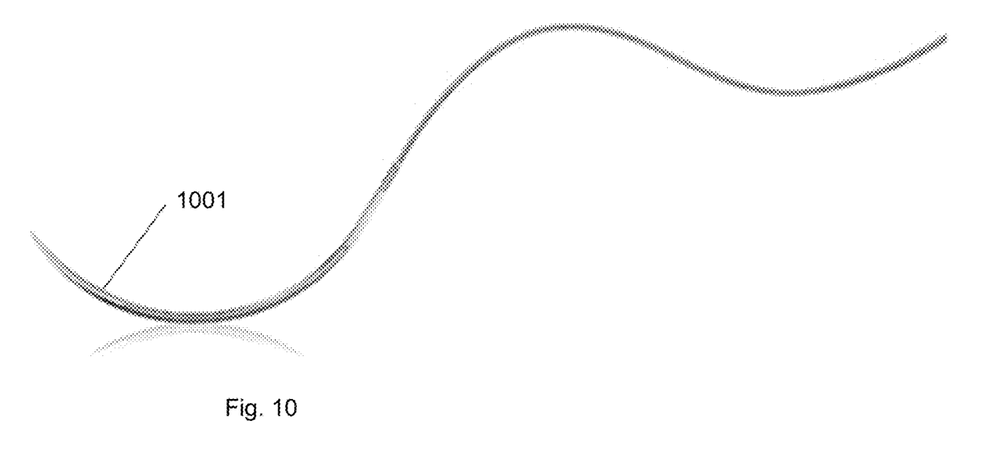
FIG. 10 illustrates a suture needle coupled to a filament.

A radiopaque tissue marker, as disclosed herein, can be a monofilament 701 as illustrated in FIG. 7, as opposed to a multifilament 801 as illustrated in FIG. 8, so that it has a low tissue reaction potential and can permanently be implanted in a patient. The filament may have a circular cross-section 901 as illustrated in FIG. 9. A radiopaque tissue marker can be incorporated into a fixation device, such as suture or tissue anchor, or a medical device implant. The radiopaque tissue marker or a device incorporating a radiopaque tissue marker can permanently remain in the patient's body, or can temporarily remain in the patient's body. A radiopaque tissue marker can be placed in either soft tissue or hard tissue sites during open, percutaneous, or endoscopic procedures. As illustrated in FIG. 2, a radiopaque tissue marker 10 can be attached to soft tissue with use of a needle 1001 as illustrated in FIG. 10, and standard surgeon's knots 12 to quickly and inexpensively mark the tissue so that the integrity and location of the marked tissue can be evaluated, A radiopaque marker can also be placed into bone with or without a hone anchor Placement of a radiopaque tissue marker can be done in a quick and reliable manner that provides for a means for marking tissue so that the integrity and location of the marked tissue can be evaluated. A radiopaque tissue marker can remain at the site of implantation with no migration over time. A radiopaque tissue marker is low profile, flexible, and continuous and facilitates outlining of a region of interest. In certain aspects, a radiopaque tissue marker can comprise an approximately 36 inch radiopaque monofilament and can be cut and multiple tissue locations can be marked with corresponding surgeon's knots. Because a radiopaque tissue marker is flexible and has a small diameter, the only portion of the marker that has the potential to be felt is the knotted portion of the marker. This portion is still much more flexible and compliant than a metallic tissue marker. A radiopaque tissue marker is able to deform somewhat to the forces placed upon it by the surrounding tissue, while remaining fixed in its location with respect to the tissue that it marks. Therefore, the tissue marker is much less likely to be felt and cause pain/discomfort to the patient.

A radiopaque tissue marker allows tissue locations to be marked via radiographic imaging with a marker that is small, yet remains visible in low-dose CT scans as well as in standard radiographs. Other commercially available tissue markers can obscure surrounding areas radiographically due to the bloom effect or deflect/deform surrounding soft tissue due to their larger size. A radiopaque tissue marker avoids these problems by being a low profile polymeric monofilament, such as a polypropylene monofilament, infused with a radioactive material, such as barium sulfate with an added dye, such as copper phthalocyanine blue cu-phthalocyanine dye, for improved visibility. A radiopaque tissue marker has a length, such as, for example, approximately 36 inches, to allow the radiopaque tissue marker to be used with arthroscopic/endoscopic cannulas, knot pushers, standard suture passers, as well as open procedures.

As stated above, a radiopaque tissue marker, as disclosed herein, provides favorable radiopacity, high tensile strength, and knot strength properties that permits placement in tissue to prevent migration. Using a tissue marker that doesn't migrate, can provide greater certainty in the boundaries of the tissue or biopsy. A surgeon can pass the tissue marker through the tissue to be marked and tie a knot with several throws. As such, the tissue marker is "sutured" in placed so that it does not migrate. Increased confidence in the biopsy boundaries can allow more patients to meet the smaller total biopsy size and margin guidelines required for accelerated partial breast irradiation (APBI) treatment, a radiation treatment course that is 5 days long rather than the standard once a week visit for 5 to 7 weeks for whole breast irradiation treatment. APBI saves cost for the treatment, cost for the patient in time/travel, and can result in better cosmetic outcomes for the patient. In this way, a radiopaque tissue marker can help save cost both on treatment options, as well as on the actual cost of the tissue marker itself.

In an aspect, a radiopaque tissue marker is incorporated into a high volume tissue filler that can be used to fill a tissue cavity. The high volume tissue filler can be a bioresorbable sphere or disc-like collagen-tissue-polymer hybrid device configured to fill empty space left behind from breast lumpectomies, for example, or other tissue cavities. The high volume tissue filler can be manufactured either by 3D printing a honey-comb or otherwise latticed three-dimensional (e.g., spherical, elliptical, or cylindrical) object using a bioresorbable polymer (such as polylactic acid, polycaprolactone, or a hyaluronic acid fiber structure, for example. The hyaluronic acid fibers may be used to create a cloth-like sheet that would likewise be resorbable) and subsequently coating the surface of the object with a collagen coating, for example. If the hyaluronic acid fiber needs to be coated with collagen, this coating may be placed by dipping the object into a collagen slurry and lyophilizing or by coating the surface with a collagen powder using a fibrin glue adhesive or similar adhesive, for example. Alternatively, a high volume tissue filler can be formed by taking a xenograft tissue extracellular matrix (ECM) sheet and rolling or folding the sheet such that the ECM becomes a volume-filling scaffold, for example. Hyaluronic acid may be applied to the xenograft tissue ECM in electrospun or medical textile form. This sheet can be sutured with a radiopaque tissue marker to maintain a shape. Alternatively, a radiopaque tissue marker can be part of a kit including the sheet and the user can use the marker to fix the shape desired and suture the sheet into a lumpectomy cavity or other hollowed tissue cavity. In other words, a high volume tissue filler can be sutured into a lumpectomy cavity with a radiopaque tissue marker. The radiopaque tissue marker can be placed at the six edges of the high volume tissue filler, for example, such that the markings can be used to denote the limits of both instances of the high volume tissue filler (the coated resorbable polymer or rolled/folded tissue) and allow radiographic visualization of a lumpectomy cavity and facilitate image guided radiotherapy or APBI as well.

A high volume tissue filler has the advantage that upon implantation, the collagen and tissue ECM can expand slightly to better fill a lumpectomy cavity or other hollowed tissue cavity. The collagen and tissue can also function to recruit native cells to heal the cavity and restore the tissue anatomy. A high volume tissue filler addresses poor cosmetic outcomes following breast lumpectomy by filling the lumpectomy volume to maintain breast shape.

Aspects of the present disclosure include high volume tissue filler kits that include a selection of different shapes and volume sizes, allowing the high volume tissue fillers to be implanted and prevent a sunken appearance in the breast where the lumpectomy occurred, for example. The incorporation of a radiopaque tissue marker to attach and mark the margins of a lumpectomy cavity can allow easier imaging of the lumpectomy cavity radiographically. The folded/rolled tissue embodiment of a high volume tissue filler can be easily modified by the user to better fit the cavity (by cutting off excess sheet material, or by rolling/folding the sheet) so as to increase the displaced volume by the implant.

In another aspect, a radiopaque tissue marker is incorporated into a surgical mesh, such as a hernia mesh. The mesh can utilize the radiopaque tissue marker as a weave or knit throughout the mesh or can use the radiopaque tissue marker primarily to mark the borders of the mesh and the center of the mesh. This can allow the mesh, such as a hernia mesh to be visualized radiographically which can facilitate placement of the mesh fluoroscopically and can be used to track hernia repair. Software can be used to track changes of the markers in the hernia mesh or other surgical mesh over time to yield information about potential hernia mesh migration/premature failure and hernia healing/repair.

In another aspect, the radiopaque tissue marker is resorbable. The marker can include iodine, for example, a radiopaque material and can be compounded into a resorbable polymer, such as polycaprolactone, for example, that resorbs at various speeds depending on its molecular weight. A biocompatible, safe colorant can be used to color the resulting compounded resin. This resin can then be extruded into a monofilament and used similar to a non-resorbable radiopaque tissue marker, except that this marker would resorb over a period of months or years. A resorbable radiopaque marker has the same advantages as a non-resorbable radiopaque marker, but has the addition of being resorbable and thus not being a lifetime permanent implant.

Figure 6:
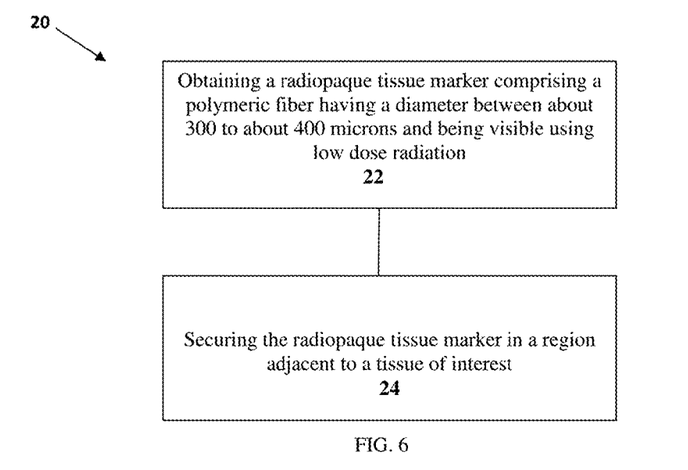
FIG. 6 is a process block diagram outlining steps of a method according to an aspect of the present disclosure.

Referring to FIG. 6, the present disclosure provides a method 20 of outlining or marking a region of tissue in a patient comprising obtaining a polymeric fiber having a diameter between about 300 to about 400 microns and being visible using low dose radiation (22). The method further comprises securing the radiopaque tissue marker in a region adjacent to a tissue of interest (24). In instances where the radiopaque tissue marker is incorporated into a suture, the method can further include tying and knotting the suture in the region adjacent to the tissue of interest. The method can further include visualizing the tissue of interest in two-dimensional space or three-dimensional space. The methodology can be used in image-guided radiation therapy.

EXAMPLES

Materials and Methods

A radiopaque tissue marker was produced using the below-described method. Compounding of the materials was performed using a twin extruder. The material composition by weight was as follows: polypropylene 54.90%+ 3.00%, barium sulphate: 44.90%+3.00%, and Cu-phthalocyanine blue 15:3: (0.2%+0.02%). The compound was then pelletized via a strand pelletizer. Extrusion was performed using monofilament fiber extrusion equipment commonly used for medical grade suture material. A fiber diameter consistent with a USP suture designation of 0 in the range of 300 to 400 microns was processed. Two separate lots of fiber material were processed. Each of the lots was tested and characterized for denier, diameter, tensile strength, elongation at rupture, and knot strength as indicated by Table I.

TABLE I

| Characteristic/Test | Example 1A | Example 1B |
|---|---|---|
| Decitex (dtex) | 1183 | 1193 |
| Diameter (microns) | 378 | 381 |
| Tensile strength (N) | 28.7 | 29.4 |
| Elongation at rupture (%) | 28 | 34 |
| Knot strength (N) | 24.0 | 26.0 |

Radiopacity and Imaging Characteristics

Figure 3:
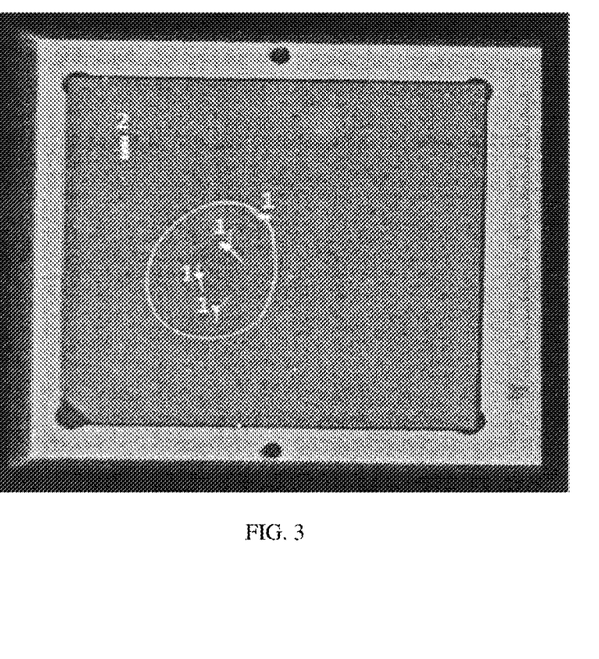
FIG. 3 is a mammography image of a Gammex MAMMO 156 phantom (28 kV, 87 mAs) containing four radiopaque tissue markers according to an aspect of the present disclosure (1) and one CASSI BEACON tissue marker (2).
Figure 4A:
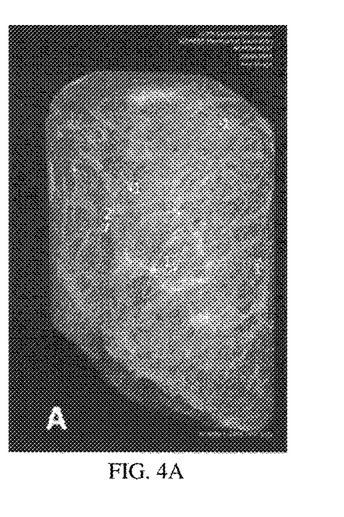
FIG. 4A is a standard mammogram (26 kV, 69 mAs) of human cadaver breast tissue containing four radiopaque tissue markers according to Example 1 of the present disclosure (1) and one CASSI BEACON tissue marker (2).
Figure 4B:
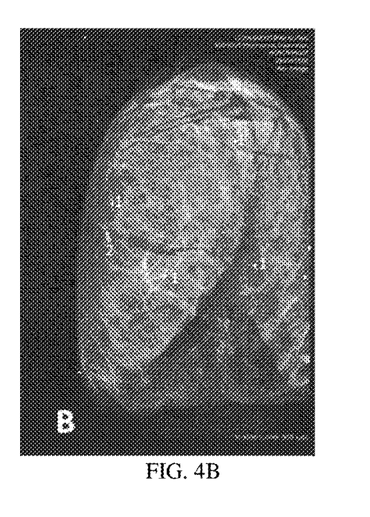
FIG. 4B is a standard mammogram (28 kV, 92 mAs) of human cadaver breast tissue containing four radiopaque tissue markers according to Example 1 of the present disclosure (1) and one CASSI BEACON tissue marker (2).

The radiopaque tissue markers from Example 1B were imaged on a Siemens Mammomat Inspiration scanner (pixel array: 2816×3584, 85 μm in plane pixel resolution) used in mammography. Markers of Example 1B were visible in a standard breast phantom and in a cadaver breast. The following parameters for the scans were as follows: phantom Scan (28 kV, 87 mAs) depicted in FIG. 3; cadaver Scan 1 (26 kV, 69 mAs) depicted in FIG. 4A; and cadaver Scan 2 (28 kV, 92 mAs) depicted in FIG. 4B. Radiopaque tissue markers of Example 1 were visible in all scans as knotted markers and as a running suture.

Figures 5A, 5C:
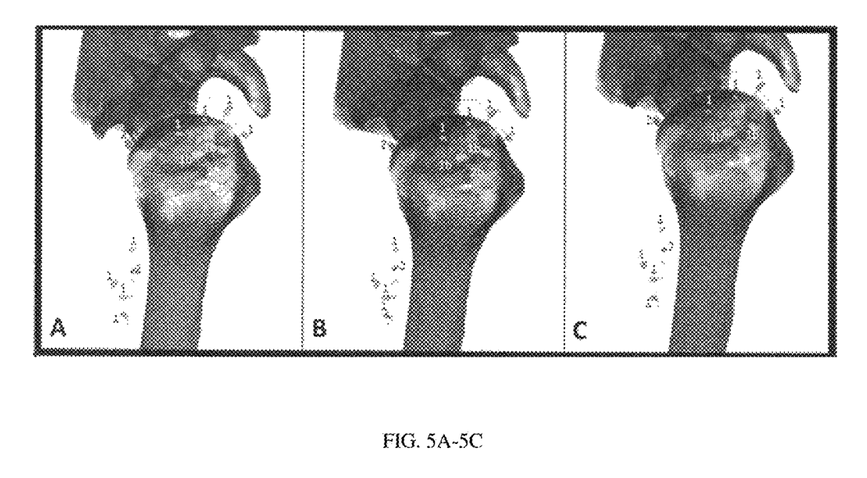

The radiopaque tissue markers of Example 1B were imaged on a Siemens SOMATOM Definition Edge scanner (CT scanner) having 64 detectors with 128 channels (voxel size: 0.5 mm×0.5 mm in-plane resolution with 0.6 mm slice thickness). Three separate CT scan doses were performed to determine the visibility at different CT energy levels. FIG. 5A-5C are computer tomography (CT) images at three separate CT scan doses of human cadaver shoulder containing ten radiopaque tissue markers according to Example 1B of the present disclosure (1, 1b) and three CASSI BEACON tissue markers (2). FIG. 5A illustrates a low-dose CT scan (100 kV, 45 mAs), where the radiation dose (0.6 mSv) is less than a standard x-ray). FIG. 5B illustrates a medium-dose CT scan (120 kV, 200 mAs), which is used clinically for soft tissue imaging. FIG. 5C illustrates a high-dose CT scan (140 kV, 300 mAs), which is used routinely for clinical imaging of shoulder implants and is one of the highest doses used clinically. The radiopaque tissue markers of Example 1B were visible in both soft tissue and within bone (placed into a pre-made hole using a 5 mm punch) and without any imaging artifacts caused by the markers.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

What is claimed is:

1. A non-biodegradable radiopaque marker comprising:
a non-biodegradable elongate flexible polymer monofilament comprising polypropylene; and
a radiopaque material disposed in the non-biodegradable elongate flexible polymer monofilament and configured to make the non-biodegradable elongate flexible polymer monofilament radiopaque,
wherein at least a portion of the non-biodegradable elongate flexible polymer monofilament is configured to be knotted and attached to tissue, and at least a portion of the non-biodegradable elongate flexible polymer monofilament is configured to be disposed along a surface of tissue so that the non-biodegradable elongate flexible polymer monofilament forms a continuous radiopaque marking,
wherein the non-biodegradable elongate flexible polymer monofilament has a circular cross-section with a diameter from 300 microns to 400 microns,
wherein the radiopaque material comprises barium sulfate having a weight of 40% or more of a total weight of the marker,
wherein the non-biodegradable radiopaque marker has a tensile strength of greater than 20 N, and
wherein the radiopaque marker is configured to be visible under radiographic imaging performed in a region ≤120 kV.

2. The marker of claim 1, wherein a portion of the non-biodegradable elongate flexible polymer monofilament comprises a knot having a tensile strength of 20 N.

3. The marker of claim 2, wherein the knot is configured to secure the radiopaque marker to tissue and prevent movement thereof.

4. The marker of claim 1, further comprising a dye or colorant disposed in the non-biodegradable elongate flexible polymer monofilament, the dye or colorant configured to enhance visibility of the radiopaque marker.

5. The marker of claim 4, wherein the dye or colorant is configured to color the radiopaque marker blue.

6. The marker of claim 1, further comprising a suture needle coupled to the non-biodegradable elongate flexible polymer monofilament.

7. The marker of claim 1, wherein the non-biodegradable elongate flexible polymer monofilament is configured to be sutured to the tissue.

8. The marker of claim 1, wherein the radiopaque marker is configured to be secured in a region adjacent to a tissue of interest.

9. The marker of claim 1, wherein the radiopaque marker does not include a high volume tissue filler configured to fill a tissue cavity.

10. The marker of claim 1, wherein the radiopaque marker is configured so that the marker does not fill a tissue cavity.

11. The marker of claim 1, wherein the non-biodegradable radiopaque marker comprises only a single non-biodegradable elongate flexible polymer monofilament.

12. A non-biodegradable radiopaque marker consisting of:
a non-biodegradable elongate flexible polypropylene monofilament;
a dye or colorant disposed in the non-biodegradable elongate flexible polypropylene monofilament, the dye or colorant configured to enhance visibility of the radiopaque marker; and
a radiopaque material disposed in the non-biodegradable elongate flexible polypropylene monofilament and configured to make the non-biodegradable elongate flexible polypropylene monofilament radiopaque,
wherein at least a portion of the non-biodegradable elongate flexible polypropylene monofilament is configured to be knotted and attached to tissue, and at least a portion of the non-biodegradable elongate flexible polypropylene monofilament is configured to be disposed along a surface of tissue so that the non-biodegradable elongate flexible polypropylene monofilament forms a continuous radiopaque marking, wherein the non-biodegradable elongate flexible polypropylene monofilament has a circular cross-section with a diameter from 300 microns to 400 microns, wherein the radiopaque material comprises barium sulfate having a weight of 40% or more of a total weight of the marker, wherein the non-biodegradable radiopaque marker has a tensile strength of greater than 20 N, and wherein the radiopaque marker is configured to be visible under radiographic imaging performed in a region ≤120 kV.

13. The marker of claim 12, wherein the radiopaque marker is configured to be secured in a region adjacent to a tissue of interest.

14. The marker of claim 12, wherein the radiopaque marker is configured to so that the marker does not fill a tissue cavity.

15. The marker of claim 12, wherein the dye or colorant is configured to color the radiopaque marker blue.

* * * * *